(12) United States Patent
Prasad

(10) Patent No.: US 6,756,012 B2
(45) Date of Patent: Jun. 29, 2004

(54) HIGH EXPANSION DENTAL ALLOYS

(75) Inventor: Arun Prasad, Cheshire, CT (US)

(73) Assignee: Jeneric/Pentron, Inc., Wallingford, CT (US)

( * ) Notice: Subject to any disclaimer, the term of this patent is extended or adjusted under 35 U.S.C. 154(b) by 0 days.

(21) Appl. No.: 09/927,940

(22) Filed: Aug. 10, 2001

(65) Prior Publication Data

US 2002/0041820 A1 Apr. 11, 2002

Related U.S. Application Data

(60) Provisional application No. 60/224,306, filed on Aug. 10, 2000, and provisional application No. 60/275,539, filed on Mar. 13, 2001.

(51) Int. Cl.$^7$ ............................................. C22C 19/07
(52) U.S. Cl. ....................................... 420/436; 148/425
(58) Field of Search ........................... 420/436; 147/425

(56) References Cited

U.S. PATENT DOCUMENTS

| | | | |
|---|---|---|---|
| 3,399,058 A | | 8/1968 | Roush |
| 4,108,642 A | * | 8/1978 | Chiaramonte ............... 420/452 |
| 4,207,381 A | * | 6/1980 | Aisaka et al. ............... 428/619 |
| 4,255,190 A | | 3/1981 | Prosen |
| 4,459,263 A | | 7/1984 | Prasad |
| 4,483,821 A | | 11/1984 | Prasad |
| 4,491,561 A | | 1/1985 | Mann |
| 4,514,359 A | | 4/1985 | Andrews |
| 4,530,664 A | * | 7/1985 | Prasad et al. ............... 420/436 |
| 4,606,887 A | | 8/1986 | Hausselt |
| 4,728,495 A | * | 3/1988 | Rademacher ............... 420/436 |
| 5,039,574 A | * | 8/1991 | Kulmburg ................... 420/436 |
| 5,154,885 A | | 10/1992 | Czech |
| 2001/0012491 A1 | * | 8/2001 | Strietzel ..................... 420/452 |

FOREIGN PATENT DOCUMENTS

| | | |
|---|---|---|
| EP | 1 122 326 | 8/2001 |
| FR | 2733416 | 4/1995 |
| FR | 2750858 | 7/1996 |
| FR | 2750867 | 4/1997 |

* cited by examiner

*Primary Examiner*—Roy King
*Assistant Examiner*—Harry D Wilkins, III
(74) *Attorney, Agent, or Firm*—Ann M. Knab

(57) ABSTRACT

Chromium-cobalt alloys useful for use with high-expansion porcelains in the fabrication of prosthetic dental appliances. The alloys herein comprise cobalt, chromium and manganese as essential components; and include one or more of aluminum, indium, gallium, tin, and germanium; and may include one or more of iron, nickel, palladium and platinum. Optional components include gold, tantalum, niobium, molybdenum, tungsten, vanadium, iridium, ruthenium, rhenium, titanium, silicon, copper, zirconium, hafnium, boron, yttrium, and rare earths metals. The alloys herein are useful with high-expansion dental ceramics and porcelains.

13 Claims, No Drawings

HIGH EXPANSION DENTAL ALLOYS

CROSS-REFERENCE TO RELATED APPLICATIONS

This is application claims priority to U.S. Provisional Application No. 60/224,306 filed Aug. 10, 2000 and U.S. Provisional Application No. 60/275,539 filed Mar. 13, 2001 which are incorporated herein by reference.

FIELD OF THE INVENTION

This invention relates to high expansion cobalt-chrome-based dental alloys.

BACKGROUND OF THE INVENTION

Gold-based alloys in dentistry were initially replaced by more economical palladium-based alloys. Recent increases in the price of palladium are making these alloys very expensive. Other economical alternatives have been nickel-based, cobalt-based and titanium-based systems. Nickel-based alloys allegedly have sensitivity and toxicity concerns. Titanium-based alloys are difficult to process and require special care and expensive equipment. These alloys, while being thermally compatible with conventional porcelains are not compatible with many high expansion porcelains available today. Although gold-based alloys are being marketed for use with high expansion porcelains, no economical alternatives exist. Metal free ceramic/composite systems and sintered or plated copings have also been used, but may lack the strength and other properties inherent in metals and alloys which render metals and alloys more desirable than their ceramic counterparts.

Thus, there is need for developing non-allergenic cobalt-based alloys to fill this void that exhibit many of the properties of precious metal alloys heretofore considered desirable in the fabrication of porcelain-veneered bridgework and crowns.

SUMMARY OF THE INVENTION

These and other objects and advantages are accomplished by the present invention which provides chromium-cobalt alloys which are significantly different from chromium-cobalt alloys heretofore employed in the fabrication of prosthetic dental appliances. The alloys herein exhibit greatly improved oxidation resistance thereby facilitating the formation of a tenacious bond with high-expansion porcelain. The alloys herein comprise cobalt, chromium and manganese as essential components and include one or more of aluminum, indium, gallium, tin, and germanium, and may include one or more of iron, nickel, palladium and platinum. Optional components include gold, tantalum, niobium, molybdenum, tungsten, vanadium, iridium, ruthenium, rhenium, titanium, silicon, copper, zirconium, hafnium, boron, yttrium, and rare earths metals. The alloys herein are useful with high-expansion dental ceramics and porcelains, most preferably with those recently introduced to the market in the range of about range from 14 to $18.5 \times 10^{-6}$.

DESCRIPTION OF THE INVENTION

The cobalt-chromium alloys of the present invention are especially suited for use in the fabrication of prosthetic dental appliances since the cobalt in the alloy imparts characteristics to the alloy which closely correspond to those of alloys having a high precious metal content. Cobalt is the major component, imparting to the alloy its inherent corrosion and tarnish resistance. The chromium in the alloy enhances this resistance. Chromium also acts as a solid solution strengthener and provides a convenient means of adjusting the thermal expansion characteristics of the alloy to conform to the variations encountered upon use of different commercial porcelains.

The cobalt-chromium alloys of the present invention comprise the following ranges of components as set forth in Table 1 below.

TABLE 1

| ELEMENTS | RANGE (WT %) | PREFERRED RANGE |
|---|---|---|
| Cobalt | about 60–about 85 | about 65–about 80 |
| Chromium | about 15–about 30 | about 18–about 25 |
| Manganese | about 2–about 20 | about 2–about 10 |
| Iron, Nickel, Palladium, or Platinum, or mixture thereof | up to about 20 | about 2–about 10 |
| Aluminum, Indium, Gallium, Tin, or Germanium, or mixture thereof | about 1–about 15 | about 1–about 7 |
| Gold | up to about 10 | about 1–about 5 |
| Tantalum, Niobium, Molybdenum, Tungsten, or Vanadium, or mixture thereof | up to about 15 | 0–about 5 |
| Iridium, Ruthenium, Rhenium, Titanium, Silicon, or Copper, or mixture thereof | up to about 6 | about 0.1–about 3 |
| Zirconium, Hafnium, Boron, Yttrium, or rare earths metals, or mixture thereof | up to about 5 | 0–about 1 |

The addition of one or more of manganese, aluminum, indium, gallium, tin, germanium has been found to increase the coefficient of thermal expansion and lower the melting temperature of the alloy. Manganese is an important component in the alloy because it is most effective in raising the coefficient of thermal expansion without embrittling the alloy, it acts as a desulfurizing agent and improves the castability of the alloy. It is preferable that manganese and aluminum are present in an amount equal to or greater than about 2%. Aluminum also improves the oxidation resistance of the alloy.

It has been found that one or more of zirconium, hafnium, boron, yttrium, and rare earths metals may be added to the alloy to function to fill lattice discontinuities that may exist at grain boundaries and thereby increase structural perfection.

The following examples in Table 2 further illustrate the criticalities of the alloy composition of the present invention. All percentages and parts are by weight.

TABLE 2

| Elements | Alloy 1 | Alloy 2 | Alloy 3 | Alloy 4 | Alloy 5 | Alloy 6 | Alloy 7 | Alloy 8 | Alloy 9 |
|---|---|---|---|---|---|---|---|---|---|
| Gold | 0 | 2 | 0 | 0 | 0 | 0 | 0 | 0 | 0 |
| Platinum | 0 | 0 | 0 | 0 | 0 | 2 | 0 | 0 | 0 |
| Cobalt | 64 | 66 | 69.9 | 69.5 | 61 | 64 | 66 | 64 | 64 |

TABLE 2-continued

| Elements | Alloy 1 | Alloy 2 | Alloy 3 | Alloy 4 | Alloy 5 | Alloy 6 | Alloy 7 | Alloy 8 | Alloy 9 |
|---|---|---|---|---|---|---|---|---|---|
| Chromium | 20 | 20 | 20 | 20 | 25 | 20 | 20 | 20 | 20 |
| Manganese | 4 | 6 | 6 | 5 | 6 | 6 | 6 | 6 | 6 |
| Aluminum | 2 | 2 | 4 | 4 | 2 | 2 | 2 | 2 | 2 |
| Gallium | 6.5 | 4 | 0 | 0 | 6 | 6 | 6 | 6 | 6 |
| Molybdenum | 3.5 | 0 | 0 | 0 | 0 | 0 | 0 | 0 | 0 |
| Tungsten | 0 | 0 | 0 | 0 | 0 | 0 | 0 | 0 | 0 |
| Indium | 0 | 0 | 0 | 0 | 0 | 0 | 0 | 0 | 0 |
| Silicon | 0 | 0 | 0 | 0.9 | 0 | 0 | 0 | 0 | 0 |
| Zirconium | 0 | 0 | 0 | 0 | 0 | 0 | 0 | 0 | 0 |
| Yttrium | 0 | 0 | 0.1 | 0.1 | 0 | 0 | 0 | 0 | 0 |
| Ruthenium | 0 | 0 | 0 | 0.5 | 0 | 0 | 0 | 0 | 0 |
| Tantalum | 0 | 0 | 0 | 0 | 0 | 0 | 0 | 0 | 0 |
| Palladium | 0 | 0 | 0 | 0 | 0 | 0 | 0 | 2 | 0 |
| Iridium | 0 | 0 | 0 | 0 | 0 | 0 | 0 | 0 | 2 |
| Total | 100 | 100 | 100 | 100 | 100 | 100 | 100 | 100 | 100 |

The thermal expansion properties of the alloys of Table 2 are provided in Table 3 below along with mechanical and other properties for alloys 2 and 7.

TABLE 3

| Properties | Alloy 1 | Alloy 2 | Alloy 3 | Alloy 4 | Alloy 5 | Alloy 6 | Alloy 7 | Alloy 8 | Alloy 9 |
|---|---|---|---|---|---|---|---|---|---|
| CTE ($\times 10^{-6}/°$ C.) (25–500° C.) | 16.22 | 16.78 | 16.52 | 16.46 | 16.18 | 16.68 | 16.9 | 16.75 | 16.63 |
| Yield Strength MPa | — | 281 | — | — | — | — | 274 | — | — |
| Ultimate Tensile Strength MPa | — | 447 | — | — | — | — | 422 | — | — |
| Hardness, $HV_5$ | — | 227 | — | — | — | — | 225 | — | — |
| Melting Range ° C. | — | 1270–1365 | — | — | — | — | 1240–1375 | — | — |

The alloys of the present invention exhibit a melting range of from about 900° C. to about 1400° C., and preferably from about 1000° C. to about 1350° C. and a coefficient of thermal expansion in the range of about 14.5 to about $19 \times 10^{-6}/°$ C. at about room temperature to about 500° C., and more preferably at about 15 to about $18 \times 10^{-6}/°$ C. at about room temperature to about 500° C. It is important that the thermal expansion is slightly higher than that of the porcelains currently available, thereby placing the porcelain under compression and minimizing stress at the interface. The thermal expansion of the alloys herein indicate that the alloys are suitable for use with high-expansion porcelains such as OPC® Low Wear™ porcelain (Jeneric®/Pentron® Incorporated) and Golden Gate porcelain (Ducera). The solidus temperature is preferably above about 800° C. and the liquidus is below about 1500° C. The most preferred melting range is 1000–1350° C.

The yield strength of the alloys herein is in excess of about 250 MPa; the tensile strength is in excess of about 400 MPa; and the elongation is in excess of about 3%. The Vickers Hardness of the alloy is no greater than about 400 $HV_5$ and preferably no greater than about 250 $HV_5$. Lower hardness imparts working characteristics similar to white precious metal alloys. The tests performed on the alloys and the properties of the alloys follow guidelines as per ISO 9693.

The alloys herein can be prepared by conventional alloying techniques. If desired, alloying can be effected in air, under vacuum or by employing a blanket of inert gas such as argon. The latter precautions, although preferred, are not considered essential. Generally, the major alloy constituents are melted first, such as through use of an induction furnace, taking care to maintain a homogeneous distribution of chromium in the melt by overcoming its tendency to float to the surface. After the cobalt and chromium have been melted and are well dispersed, the manganese can be added. Thereafter, the remaining alloy constituents can be added in either elemental form or as a preformed alloy with cobalt or chromium. Once the alloy melt is prepared and ingots cast therefrom, the remelting of the alloy ingot may be accomplished using a standard natural gas/oxygen torch or induction melting equipment.

The alloys herein are useful in the manufacture of dental restoratives including, but limited to, crowns, bridges, space maintainers, tooth replacement appliances, orthodontic retainers, dentures, posts, jackets, inlays, onlays, facings, veneers, facets, implants, abutments, splints, partial crowns, teeth, cylinders, pins, and connectors. Preferably the alloys herein are used as the core material and may be veneered with ceramic or porcelain materials, such as high-expansion porcelains.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A cobalt-chromium dental alloy comprising by weight percent:
   about 60 to about 85% cobalt;
   about 15 to about 30% chromium;
   about 4 to about 20% manganese; and
   about 1 to about 15% aluminum, indium, gallium, tin, or germanium, or mixture thereof; and
   wherein the coefficient of thermal expansion at room temperature to about 500° C. is about 16 to about $18 \times 10^{-6}$/° C.

2. The cobalt-chromium alloy of claim 1 wherein aluminum is present in an amount of at least about 2%.

3. The cobalt-chromium dental alloy of claim 1 further comprising:
   up to about 20% iron, nickel, palladium, or platinum, or mixture thereof;
   up to about 10% gold;
   up to about 15% tantalum, niobium, molybdenum, tungsten, or vanadium or mixture thereof;
   up to about 6% iridium, ruthenium, rhenium, titanium, silicon, or copper or mixture thereof; and
   up to about 5% zirconium, hafnium, boron, yttrium, or a rare earth metal or mixture thereof.

4. The cobalt-chromium dental alloy of claim 1 having a Vickers Hardness of no greater than about 300 $HV_5$.

5. A dental restoration comprising the cobalt-chromium alloy of claim 1.

6. The dental restoration of claim 5 further comprising a high-expansion porcelain on the cobalt-chromium alloy.

7. The dental restoration of claim 5 wherein the dental restoration comprises a restoration selected from the group consisting of a crown, bridge, space maintainer, tooth replacement appliance, orthodontic retainer, denture, post, jacket, inlay, onlay, facing, veneer, facet, implant, abutment, splint, partial crown, teeth, cylinder, pin, connector or combination thereof.

8. A cobalt-chromium dental alloy comprising by weight percent:
   about 65 to about 80% cobalt;
   about 18 to about 25% chromium;
   about 4 to about 10% manganese;
   about 2 to about 10%, iron, nickel, palladium, or platinum, or mixture thereof;
   about 1 to about 7% aluminum, indium, gallium, tin, or germanium, or mixture thereof;
   about 1 to about 5% gold; and
   about 0.1 to about 3% iridium, ruthenium, rhenium, titanium, silicon, or copper, or mixture thereof; and
   wherein the coefficient of thermal expansion at room temperature to about 500° C. is about 16 to about $18 \times 10^{-6}$/° C.

9. The cobalt-chromium dental alloy of claim 8 further comprising:
   up to about 5% tantalum, niobium, molybdenum, tungsten, or vanadium, or mixture thereof, and
   up to about 1% zirconium, hafnium, boron, yttrium, or a rare earth metal, or mixture thereof.

10. The cobalt-chromium dental alloy of claim 8 having a Vickers Hardness of no greater than about 300 $HV_5$.

11. A dental restoration comprising the cobalt-chromium alloy of claim 8.

12. The dental restoration of claim 11 further comprising a high-expansion porcelain on the cobalt chromium alloy.

13. The dental restoration of claim 11 wherein the dental restoration comprises a restoration selected from the group consisting of a crown, bridge, space maintainer, tooth replacement appliance, orthodontic retainer, denture, post, jacket, inlay, onlay, facing, veneer, facet, implant, abutment, splint, partial crown, teeth, cylinder, pin, connector or combination thereof.

* * * * *